(12) United States Patent
Beckman

(10) Patent No.: US 11,185,234 B2
(45) Date of Patent: Nov. 30, 2021

(54) SYSTEM AND METHOD OF USING ULTRAFAST RAMAN SPECTROSCOPY AND AN ABLATIVE LASER FOR QUASI-REAL TIME REMOVAL OF SKIN CANCER AND OTHER ANOMALOUS TISSUES WITH CLEAR TISSUE MARGINS FORMED BY ARRAY CREATED DISPLAYS

(71) Applicant: Hugh Beckman, Boca Raton, FL (US)

(72) Inventor: Hugh Beckman, Boca Raton, FL (US)

( * ) Notice: Subject to any disclaimer, the term of this patent is extended or adjusted under 35 U.S.C. 154(b) by 0 days.

(21) Appl. No.: 16/854,022

(22) Filed: Apr. 21, 2020

(65) Prior Publication Data

US 2020/0345236 A1  Nov. 5, 2020

Related U.S. Application Data

(60) Provisional application No. 62/920,468, filed on May 2, 2019.

(51) Int. Cl.

| | |
|---|---|
| *A61B 5/00* | (2006.01) |
| *A61B 18/00* | (2006.01) |
| *A61B 18/20* | (2006.01) |
| *G16H 20/40* | (2018.01) |
| *A61B 34/32* | (2016.01) |
| *A61B 18/22* | (2006.01) |
| *A61B 17/00* | (2006.01) |

(52) U.S. Cl.
CPC .......... *A61B 5/0075* (2013.01); *A61B 5/0036* (2018.08); *A61B 5/0068* (2013.01); *A61B 5/444* (2013.01); *A61B 18/22* (2013.01); *A61B 34/32* (2016.02); *G16H 20/40* (2018.01); *A61B 2017/00761* (2013.01); *A61B 2018/00577* (2013.01); *A61B 2018/00642* (2013.01); *A61B 2018/20355* (2017.05)

(58) Field of Classification Search
CPC ..... A61B 5/0075; A61B 5/0068; A61B 5/444; A61B 2018/00577; A61B 2018/20355
See application file for complete search history.

(56) References Cited

U.S. PATENT DOCUMENTS

| | | | |
|---|---|---|---|
| 4,913,142 | A | 4/1990 | Kittrell |
| 5,104,392 | A | 4/1992 | Kittrell |
| 5,304,173 | A | 4/1994 | Kittrell |
| 10,105,456 | B2 | 10/2018 | Harmsen |

(Continued)

*Primary Examiner* — Angela M Hoffa
(74) *Attorney, Agent, or Firm* — Nolte Lackenbach Siegel; Myron Greenspan

(57) ABSTRACT

Resonance Raman scatter is used to differentiate in quasi-real time (QRT) anomalous tissue from adjacent normal tissue. The fingerprint generated from the tissue by a 1 second pulse of 532 nm emission for approximately one second is collected and is relayed by fiber-optic to a computerized controller that determines whether the target tissue is anomalous or normal. If anomalous it is ablated. This is performed by a pattern of Resonance Raman diagnostic emission and diagnostic sensor fibers. This diagnostic/therapeutic pattern of fibers can be moved by a joystick or robotically controlled. The data received by the computer is examined instantly, and should the site be diagnosed as anomalous, the optical biopsy/ablation is repeated immediately and repeated until the site is read as normal. Novel arrays of the diagnostic and therapeutic energies ensure a 3D anomalous tissue free zone around the removal site.

19 Claims, 12 Drawing Sheets

(56) References Cited

U.S. PATENT DOCUMENTS

| | | | |
|---|---|---|---|
| 10,426,349 B2 | 10/2019 | Alfano | |
| 10,888,227 B2* | 1/2021 | Kircher | A61B 1/00087 |
| 2002/0045811 A1 | 4/2002 | Kittrell et al. | |
| 2009/0281536 A1* | 11/2009 | Beckman | A61B 5/444 |
| | | | 606/33 |
| 2014/0140594 A1* | 5/2014 | Mahadevan-Jansen | |
| | | | G06T 7/0012 |
| | | | 382/128 |
| 2014/0316255 A1* | 10/2014 | Garai | G01J 3/18 |
| | | | 600/424 |
| 2014/0350534 A1 | 11/2014 | Kircher et al. | |
| 2015/0018807 A1 | 1/2015 | Kircher et al. | |
| 2016/0000329 A1 | 1/2016 | Kircher et al. | |
| 2016/0000330 A1* | 1/2016 | Huang | G01J 3/0272 |
| | | | 600/476 |
| 2016/0199132 A1* | 7/2016 | Anderson | A61B 18/203 |
| | | | 606/9 |

\* cited by examiner

|   | F1 | 2 | 3 | 4 | 5 | 6 | 7 | 8 | 9 |
|---|----|----|----|----|----|----|----|----|----|
| A | 1A |    |    | 4A | 5A | 6A | 7A |    | 9A |
| B |    | 2B | 3B | 4B | 5B | 6B | 7B | 8B |    |
| C | 1C | 2C | 3C | 4C | 5C | 6C | 7C | 8C | 9C |
| D | 1D | 2D | 3D | 4D | 5D | 6D | 7D | 8D | 9D |
| E | 1E | 2E | 3E | 4E | 5E | 6E | 7E | 8E | 9E |
| F | 1F | 2F | 3F | 4F | 5F | 6F | 7F | 8F | 9F |
| G |    | 2G | 3G | 4G | 5G | 6G | 7G | 8G |    |
| H |    | 2H | 3H | 4H | 5H | 6H | 7H | 8H |    |
| I | 1I |    | 3I | 4I | 5I | 6I |    |    | 9I |

FIG. 6

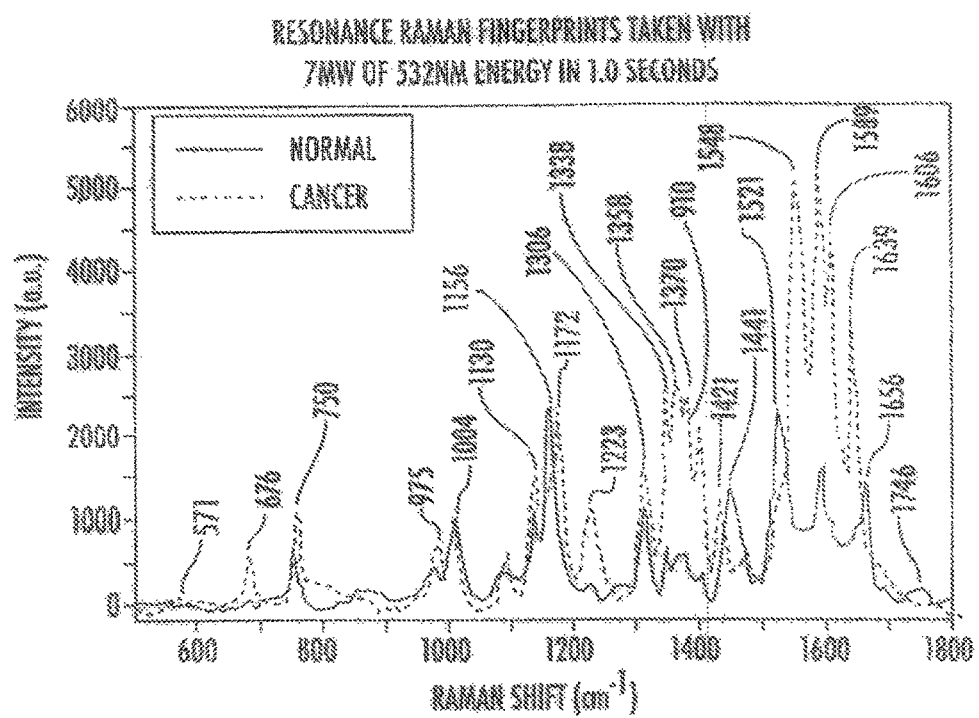

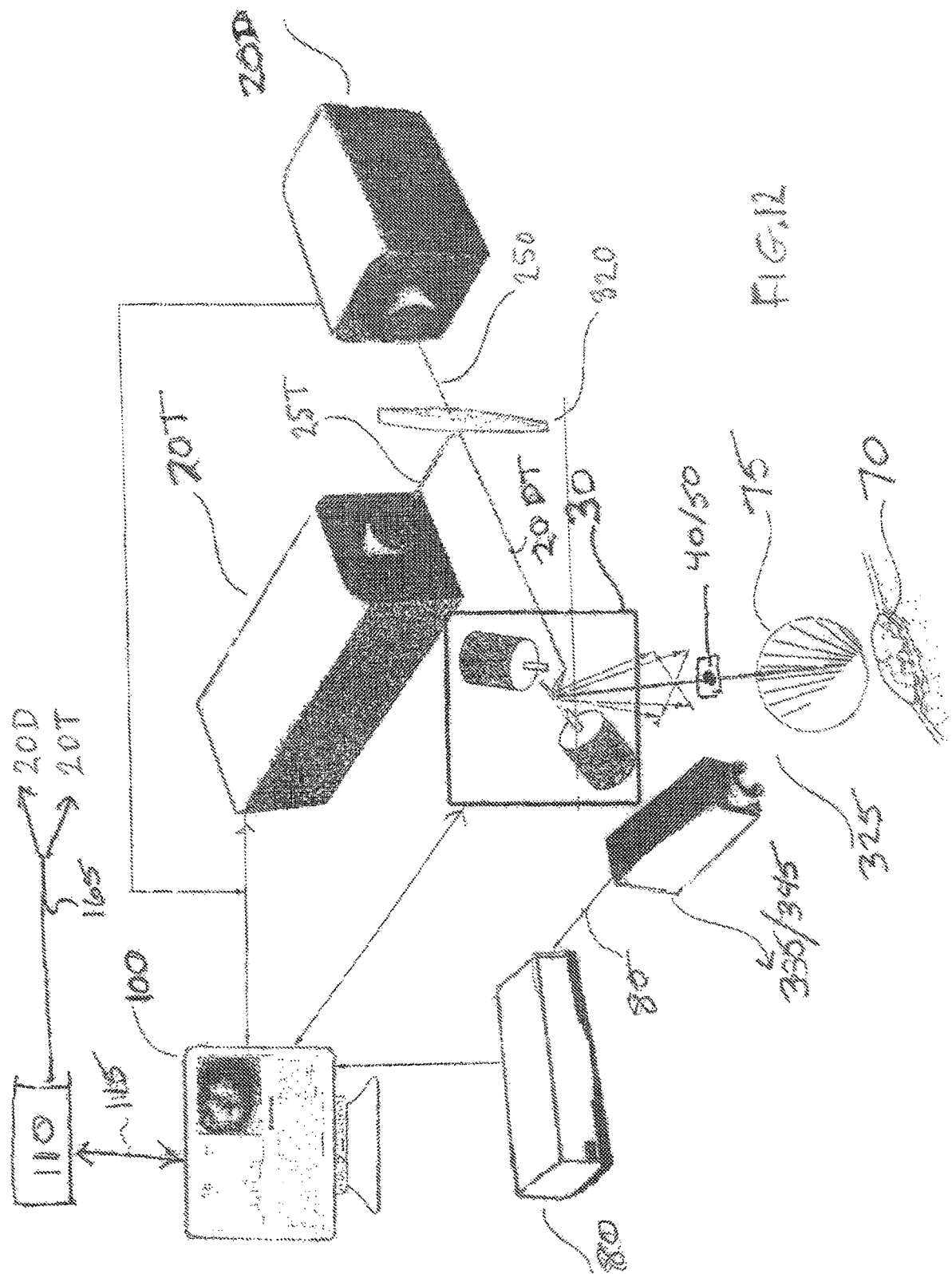

SYSTEM AND METHOD OF USING ULTRAFAST RAMAN SPECTROSCOPY AND AN ABLATIVE LASER FOR QUASI-REAL TIME REMOVAL OF SKIN CANCER AND OTHER ANOMALOUS TISSUES WITH CLEAR TISSUE MARGINS FORMED BY ARRAY CREATED DISPLAYS

CROSS-REFERENCE TO RELATED APPLICATION

This application is related to U.S. Provisional Application Ser. No. 61/051,705 filed May 9, 2008; U.S. patent application Ser. No. 12/437,589 filed May 9, 2008 and claims the benefit of priority of U.S. Provisional Application 62/920,468 filed on May 2, 2019, all of which are incorporated herein in their entirety by reference.

BACKGROUND OF THE INVENTION

1. Field of the Invention

The present invention is generally directed to devices that analyze organic and micro-organic tissue by detecting spectra, and linking those devices to a therapeutic modality for the quasi-real-time (QRT) concurrent diagnosis and treatment of abnormal tissue, and to the process of removing the anomalous tissue, creating a zone surrounding the lesion that is free of anomalous tissue in 3D. If needed, a created template could be used to custom create a graft to facilitate repair.

2. Description of the Prior Art

Surgical excision of neoplastic tumor tissue, as well as other anomalous tissues, has historically been performed manually using steel blades as well as lasers etc. In recent years, robotic devices have been used to assist the surgeon. By way of example, many surgeons advocate the use of the Mohs technique to diagnose malignant tissues of the skin. The Mohs technique includes mapping a specimen of the target tissue, staining the tissue and evaluating the tissue under a microscope to determine the amount and location of residual tumor cells. The area in question is marked for orientation and local anesthetic is used. The tissue is surgically removed in layers, divided and mapped with reference points on the patient and upon the slides of the frozen sections. These sections are analyzed histopathologically and if any area of the specimen contains anomalous tissue, the marks guide the surgeon to the precise location or locations to determine if anomalous tissue still exists. The process is then repeated until no tumor is seen on any of the subsequent surgical specimens. There are many disadvantages to this treatment system. There may be unnecessary tissue removal and cosmetic damage. Long treatment sessions may occur due to the manual microscopic viewing and assessment of each layer removed. Freezing the tissue samples may also be required which decreases the accuracy of the results. A simpler, more efficient, more accurate, and less time consuming method of diagnosis and removal of the abnormal tissue would represent a significant advance in patient care. Kittrell[1], Redd[2] and Beckman[3]. All recognized the potential of Raman Spectroscopy as a method for differentiating anomalous from adjacent normal tissue. However the time required for normal Raman to perform this task was too long to make it practical as a driver for an ablative energy to be used. Kircher and Harmson[4] has suggested injection of nanoparticles to selectively tag the tumor cells which requires the injection of toxic or potentially toxic substances into the body. Fox, Beckman[5] have shown that high-powered CO2 laser energy impinging on cancerous and normal tissues does not disturb the ability of Raman to differentiate them. And recently C. Liu, Alfano, Beckman et al have shown that a variety of ultrafast Raman designated Resonance Raman[6] and Zhou[7] could perform differentiation of basal cell carcinoma from adjacent normal tissue in one second or less, making quasi-real-time (QRT) feasible as a driver for a therapeutic entity such as, but not limited to a high-powered carbon dioxide laser for the first time[8]. This feasibility, with the methodology utilized to ensure the ability to selectively remove anomalous tissue with clear tumor free margins, and create a computerized template of the removal site in order to facilitate cosmetic repair of the margin, is the subject of this application.

[1] References 1-4
[2] Reference 5
[3] Reference 6
[4] References 7-10
[5] Reference 20
[6] Reference 15
[7] Reference 19
[8] Reference 21

SUMMARY OF THE INVENTION

Disclosed herein is an embodiment of a medical device for diagnosing and treating anomalous tissue such as, but not limited to, basal cell carcinoma, squamous cell carcinoma, other carcinomas, atheromata and micro-organisms. Such a device comprises an energy source configured to emit at least an excitation beam of radiation such as, but not limited to, 532 nm energy as needed to produce resonance Raman scattering (RRS) at the target site. This device also comprises an energy source configured to emit at least therapeutic energy, such as, but not limited to, high-powered 10.6 micron (CO2) or low powered UVC energy as needed to produce ablation of the anomalous tissue at the target site if needed. This device also has collectors to capture the induced Raman scatter and relay it to sensors that relay the scatter energy to a spectrophotometer wherein a fingerprint is generated and relayed to a computer/controller. The fingerprint thus obtained is interpreted by the computer and compared to stored database fingerprints, and if found to be anomalous triggers a therapeutic ablative energy to be delivered to the anomalous tissue. This diagnostic/therapeutic event will be completed in approximately 1 second due to the use of RRS as the diagnostic tool. Should the target site be found to be normal, the controller will either move the array of fibers to an adjacent area, or repeat a diagnostic ablation at the same area as dictated by a unique array of diagnostic energy points that serve not only to guide the energies, but uniquely provides guidance as to when a clear zone of normalcy appears as the anomalous tissue meets normal tissue, reducing the threat of recurrence due to outlying anomalous cells. The modes of energy delivery are repeated and alternately selected as needed until removal of the anomalous tissue is completed with a surrounding clear zone formed in 3-D.

Other embodiments can be found in the detailed description of embodiments of the invention.

BRIEF DESCRIPTION OF THE DRAWINGS

The following descriptions are in reference to the accompanying drawings in which the same or similar parts are referenced by the same numerals throughout the several drawings, and wherein:

FIG. 6 is a schematic of a three-dimensional array as it is represented in a computer/controller;

FIGS. 9a and 9b depict a fingerprint taken from a basal cell carcinoma specimen and from an adjacent specimen of normal tissue, both with Resonance Raman 532 nm energy in a 1.0 second pulse;

FIG. 10a is a schematic of the energies going through the array producing device into a confocal microscope creating a Raman scatter plume picked up by the sensors into the sensor device;

FIG. 10b is an enlarged view of the region A in FIG. 10a;

FIG. 12 is a rendition of the energy paths taken in the production of a diagnostic/therapeutic event, with emphasis on the creation of arrays and patterns.

DETAILED DESCRIPTION OF THE EMBODIMENTS OF THE INVENTION

In the various figures like reference numbers refer to identical or similar like parts. The figures are exemplary and are not drawn to scale.

Figure 1:
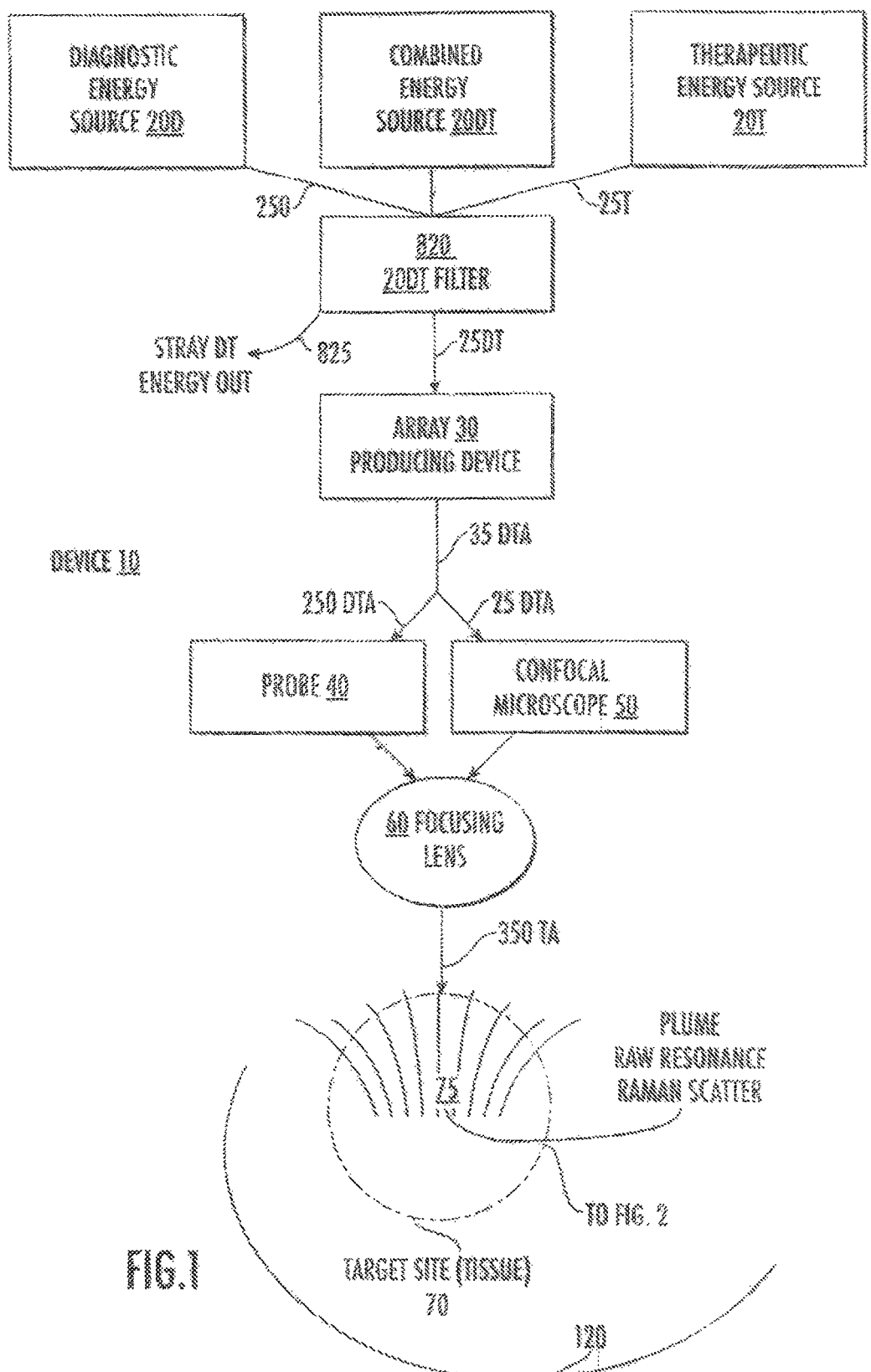
FIG. 1 is Part 1 of a schematic of one embodiment of the medical device for diagnosing and treating anomalous tissue as disclosed herein, illustrating the sequencing from the energy sources to the impact site, and is continued in FIG. 2.
Figure 2:
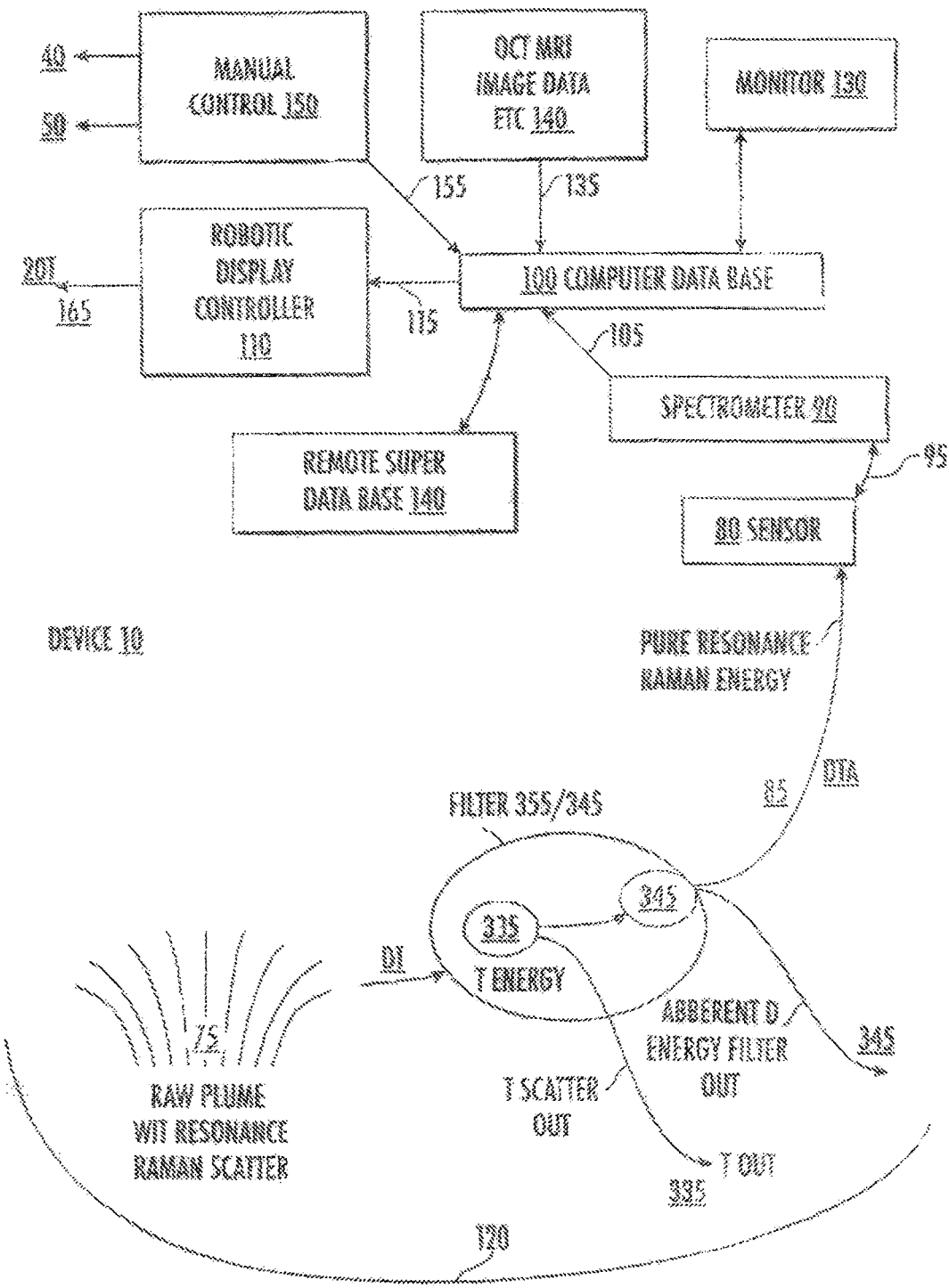
FIG. 2 is Part 2 of the schematic of the embodiment shown in FIG. 1, starting from the plume at the impact site and following the path of the Raman scatter through the devices necessary for the diagnosis and treatment of the anomalous tissue as disclosed herein.

As seen in FIGS. 1 and 2 a preferred embodiment of the medical device 10 is shown for diagnosing and treating anomalous tissue. The medical device 10 comprises a high energy source 20T (therapeutic) such as but not limited to a High Peak powered CO2 laser, and a low energy source 20D (diagnostic) energy source such as, but not limited to 532 micron energy.

Figure 8:
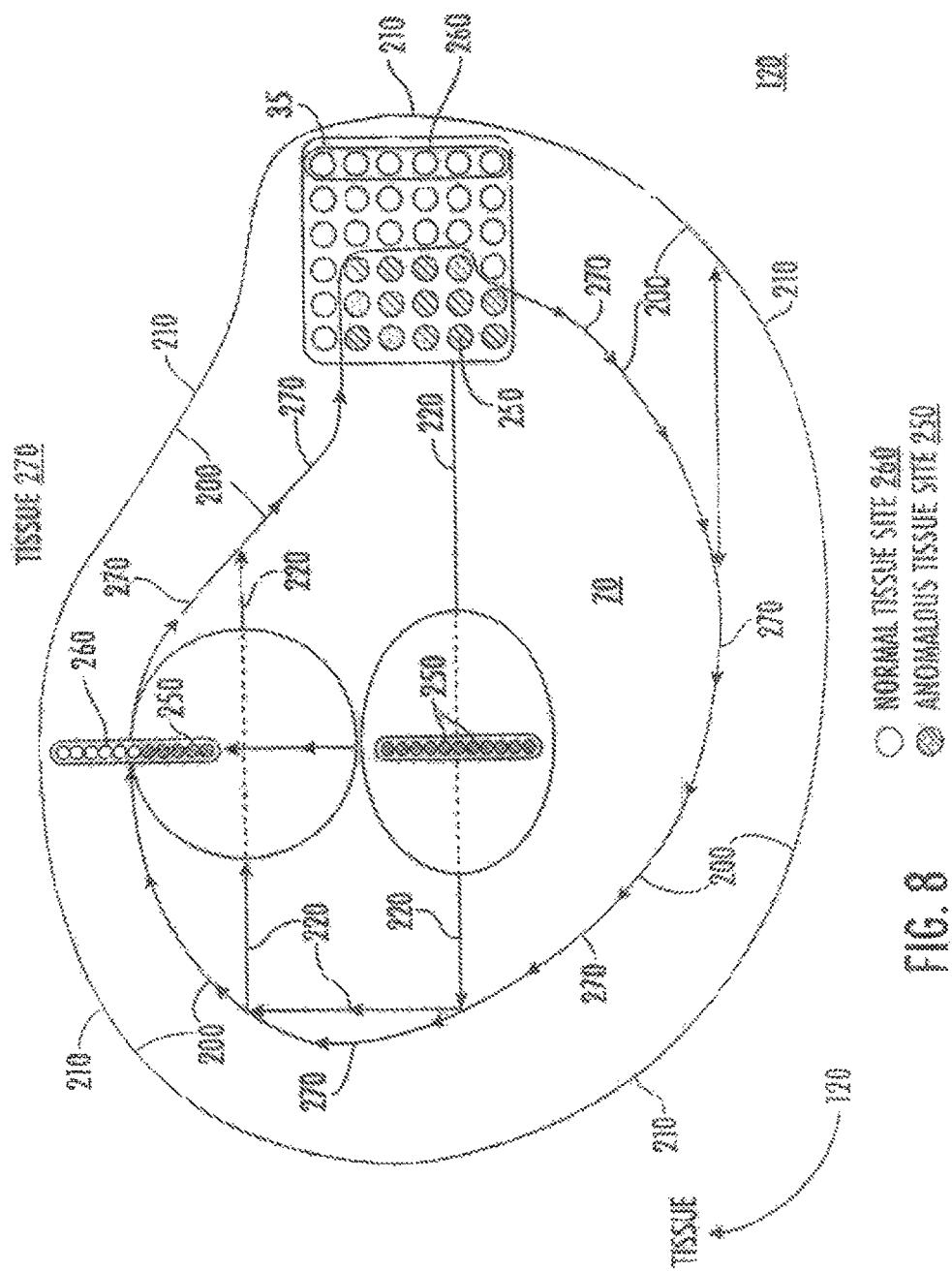
FIG. 8 illustrates two tracking patterns of the arrays: one to debulk the anomalous tissue from the outside in, and the other to create a perimeter outlining the lesion from the inside out.
Figures 10A, 10B:
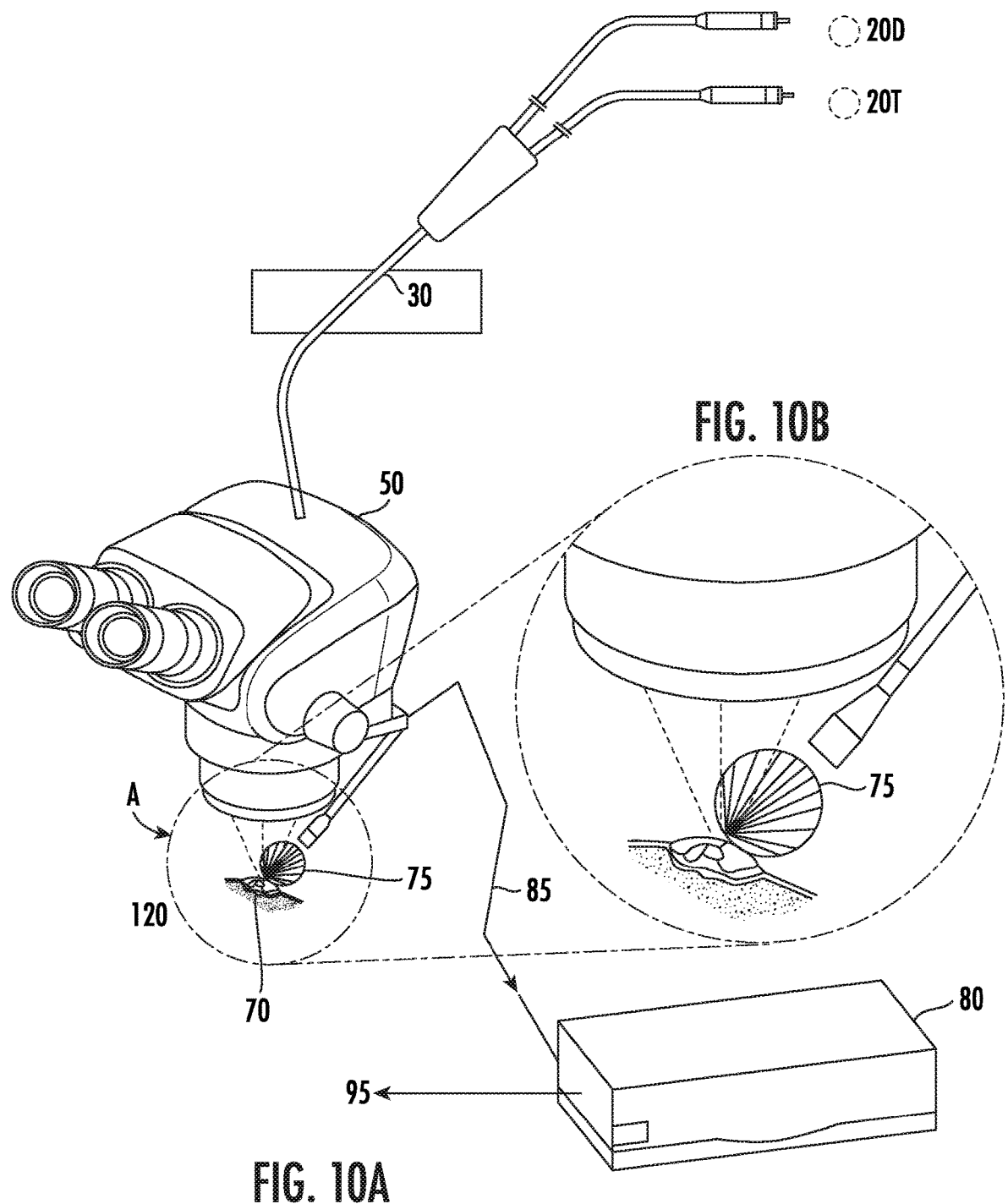
Figure 11:
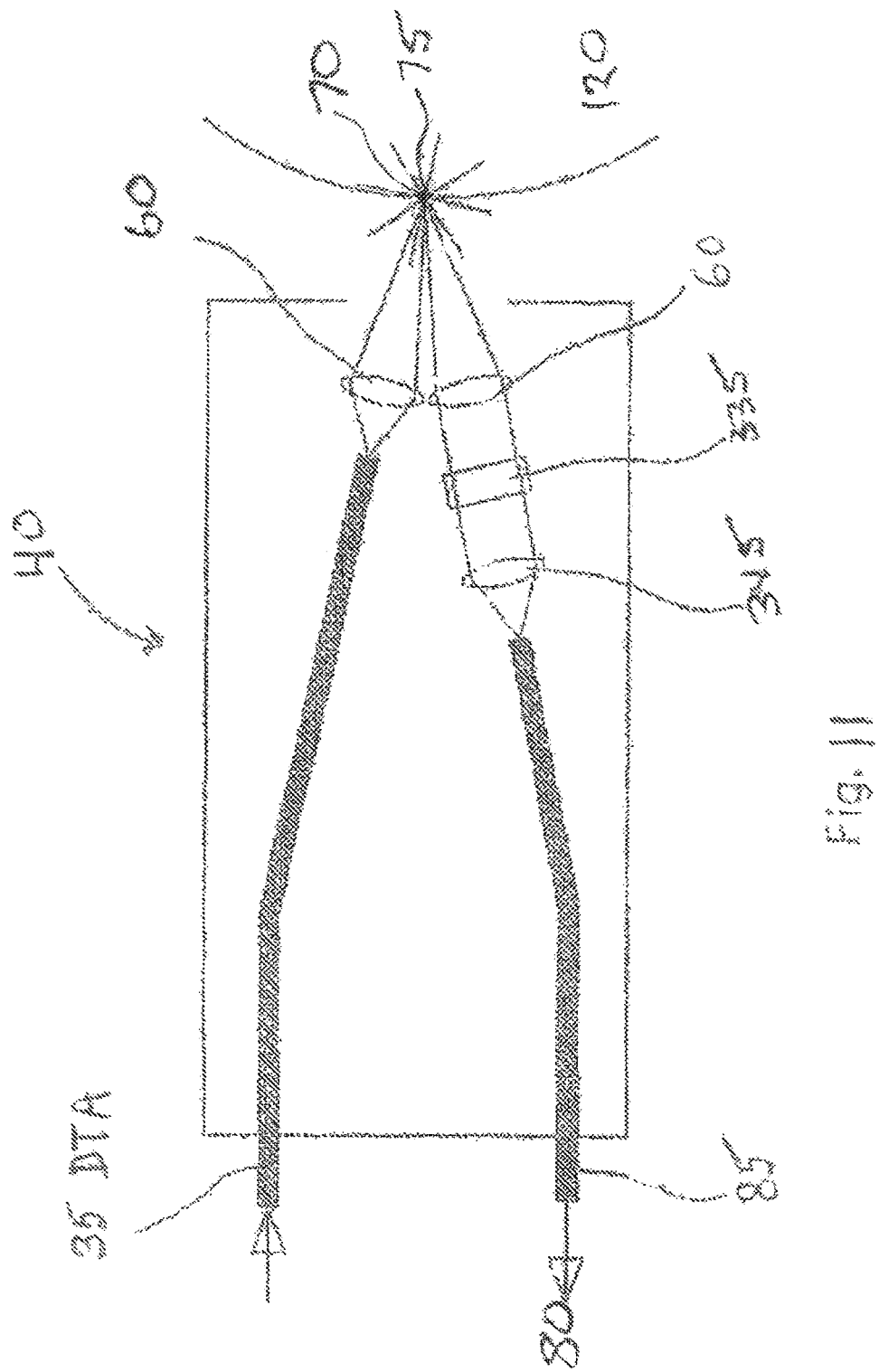
FIG. 11 is a schematic representation of the probe carrying therapeutic and diagnostic energy coaxially to the target site, resulting in Resonance Raman scatter input to the sensor after aberrant scatter has been filtered out.

These energy sources are either under either the control of a manual controller 150, or a robotic display controller 110 send energy, in this embodiment, coaxially through conduit 25 DT through filter 820 to the array producing device 30 after stray energy 825 has been filtered out. The arrays 260, 290 and 35DA, shown in FIGS. 4, 5 and 8 continue through conduit 35 DTA to either the probe 40 or confocal microscope 50. The signals in the conduit 35DTA are focused by either delivery device 40, 50 onto the target site by a focusing lens or system of lenses 60. The ablative energy creates a plume 75 containing Resonance Raman scatter as well some aberrant therapeutic scatter and diagnostic scatter, which is filtered out by lenses 335/345. Pure Resonance Raman energy is then transmitted through conduit 85 to the sensors 80 which relays it in conduit 95 to the spectrometer 90 where the array is represented as in FIG. 5. Conduit 105 conveys it to the computer 100 where the fingerprint FIG. 9 is received and a determination is made as to whether the site analyzed is anomalous or normal. Should the fingerprint be anomalous, the surgeon under manual control 150 or the robotic controller 110 triggers a pulse of ablative energy 20T onto the target site 70. If it is determined that the tissue is normal, then the surgeon under manual control at 150 or the robotic controller at 110 either sends another pulse deeper into the same site, or the site is moved to an adjacent area and the sequence repeated. In either case the sequence is repeated until all anomalous tissue is removed using a pattern, by example, as shown in FIG. 8.

As used herein, the term "anomalous" or "anomaly" refers to that tissue that it is desirable to be removed. The anomalous tissue can be, for example, cancerous or precancerous lesions, or abnormalities such as atheromata, viruses and other pathologies. If a determination is made by the computer database 100 that the fingerprint of the target tissue 70 is anomalous, the controller 110 activates the energy source 20T and the site is ablated On the visualized tissue 120 the target site 70 is selected and the diagnostic energy source 20D is triggered sending energy through filter 820 on to the array producing device 30. A surgeon can determine whether the array of diagnostic energy is directed either to the probe 40 or confocal microscope 50. From there the radiation is directed through the focusing lens 60 onto the target site 70 where is produces a plume 75 containing the Resonance Raman scatter as well as some spurious or foreign scatter. The foreign scatter Is filtered out by filters 335 and 345 and the pure Resonance Raman energy 85 is captured by the sensor 80 and relayed through conduit 95 to the spectrometer 90 from which it is input through conduit 105 to the computer data base 100 where a fingerprint of the energy is produced. Should the site be found to be anomalous a message is sent through the manual controller 150 or the robotic display controller 110 triggering a therapeutic pulse of energy from source 20T resulting in an ablation of the tissue site 70.

As used herein, an anomalous fingerprint can be a malignant fingerprint not yet ablated or an anomalous site that has been ablated but not yet rid of abnormality.

The energy source 20T delivers ablative energy to that same tissue site through the probe 40 or the microscope 50 sufficient to ablate at least a portion of the target tissue site 70. This therapeutic ablative energy 20T may be delivered in one or multiple doses as desired or required. The number, the power, and duration of the pulses may be adjusted as required to ablate the anomalous tissue. As used herein, the term "ablate" refers to effectively removing the anomalous tissue by separation, destruction, vaporization, evaporation, melting, genetic modification or the like.

In another embodiment a combined energy source 20DT can be used to replace separate energy sources 20D and 20T to deliver both the diagnostic and the excitation beam and the therapeutic beam. Such energy source may be, for example but not limited to a frequency doubled Nd:YAG laser emitting 532 nm energy, with suitable power configurations such as but not limited to continuous wave, pulsed high peak power lasers, femto second lasers and other electromagnetic energy forms. Energy sources are not limited to light sources such as lasers and can be any other electromagnetic source known to those skilled in the art that is sufficient to achieve the results desired. One or more lenses can be used to focus the therapeutic laser energy at the target tissue to be ablated.

Figure 3:
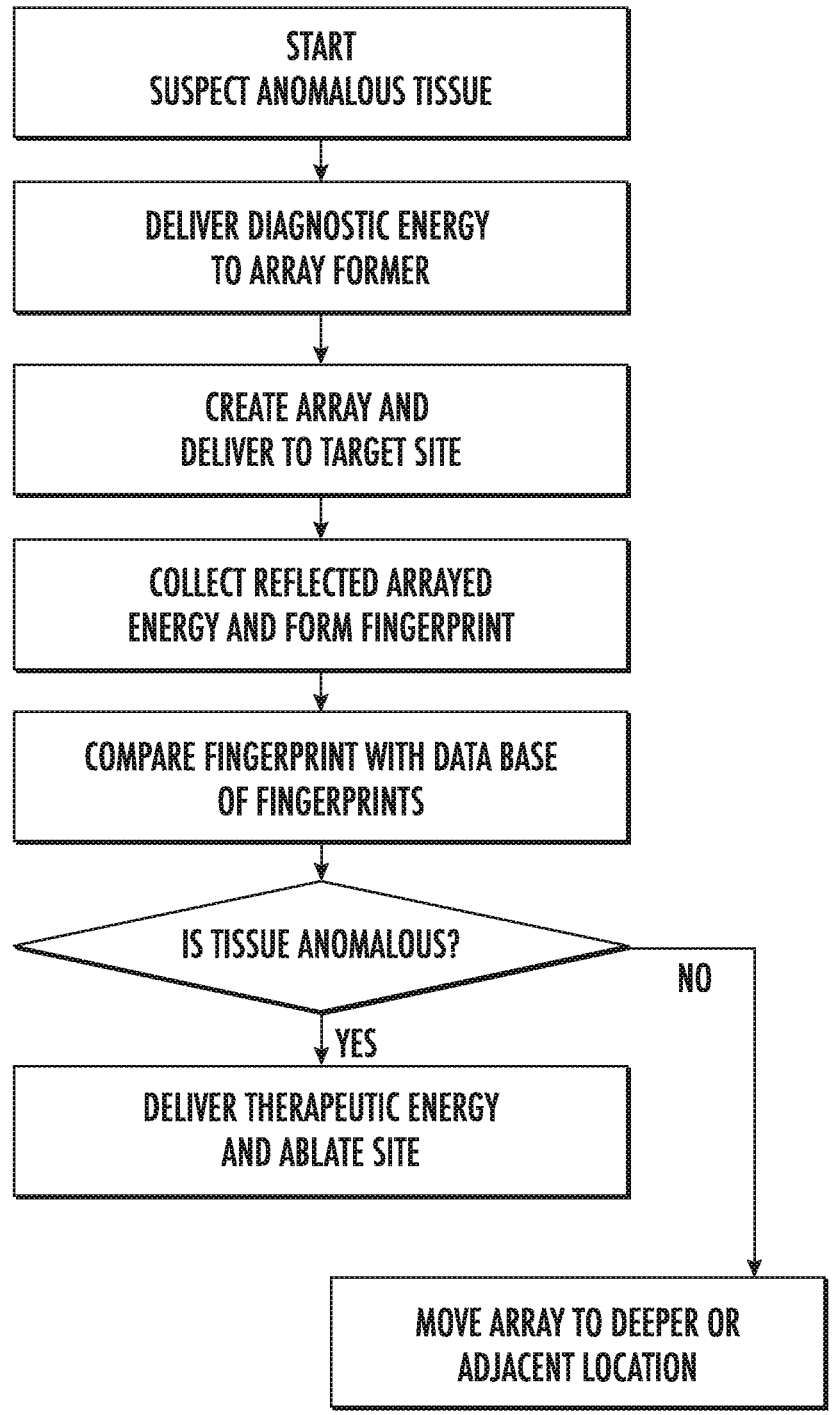
FIG. 3 is a flow chart detailing the logical functions during the usage of the medical device embodied in FIGS. 1 and 2.

If it is determined that the fingerprint 105 of the target tissue 70 is normal the procedure can proceed differently depending on the required result. The array of either the probe 40 or the microscope 50 can be moved to the next location. The subsequent target site may be deeper at the same site or to an adjacent site. The procedure is illustrated by the flow chart shown in FIG. 3.

Figure 7:
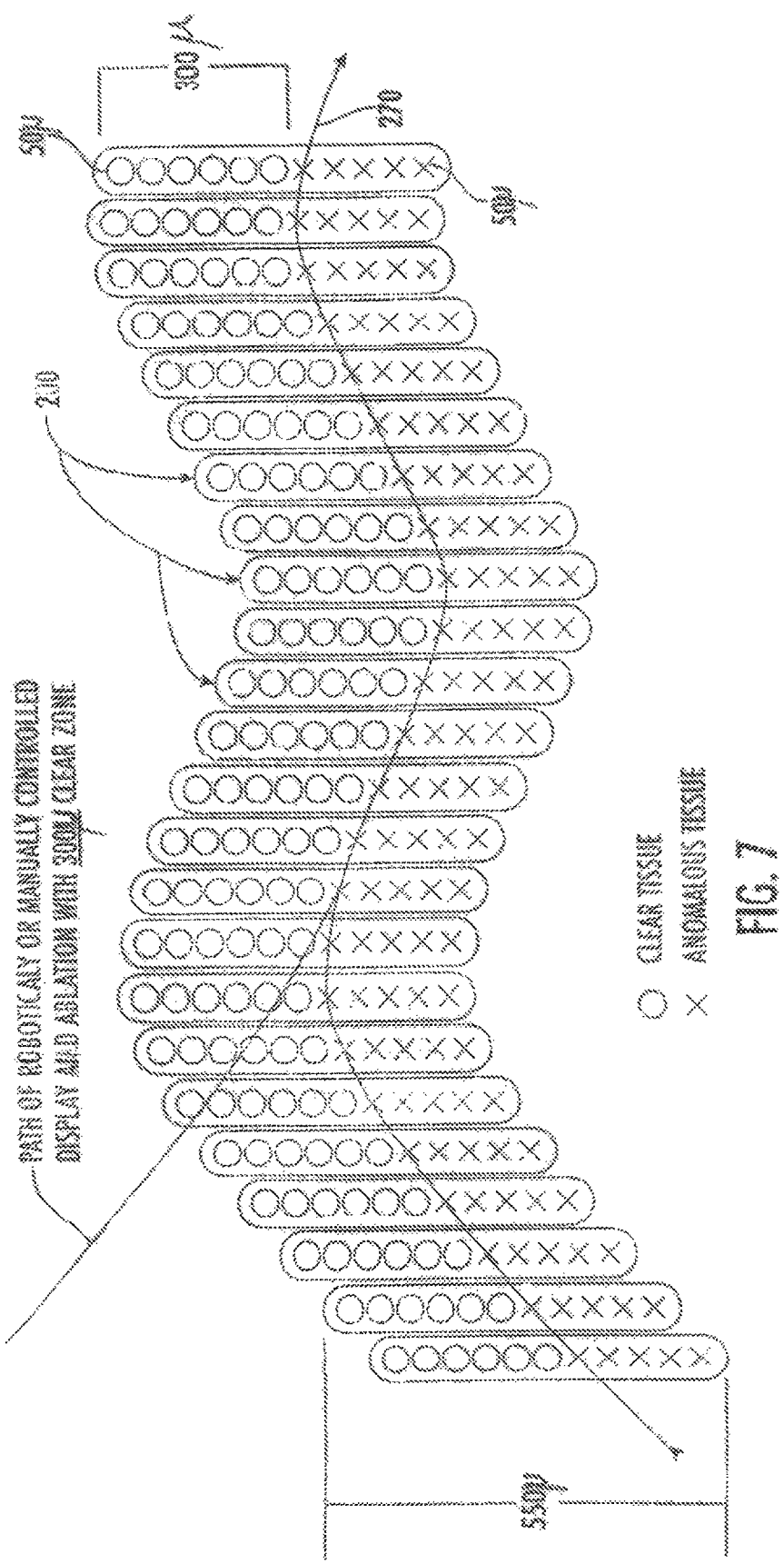
FIG. 7 schematically depicts the path of a robotically or manually controlled display with diagnosis and ablation resulting in a 300 Micron zone clear of anomalous tissue.

Utilizing the patterns formed by the arrays depicted in FIGS. 5, 6, 7, and 8, the direction of the excitation, the Resonance Raman scatter, and ablative beam as necessary will be relayed after fingerprint interpretation to the robotic display controller 110 and the appropriate location correction for the target site 70 made. All the arrays noted above are designed in a manner that creates by way of example, at least a 300μ region of contiguous free anomalous tissue sites in the same horizontal or depth path as seen in FIG. 7. Thus a zone at least 300μ wide free of anomalous tissue will be created in 3-D multiple passes at different depths until all anomalous tissue is removed.

It may be necessary to diagnose remaining target tissue 70 after the therapeutic ablation or to diagnose tissue below a tissue layer. A decision can then be made by the robotic display controller 110 or the surgeon to deliver ablative energy to the same target tissue 70 rather than move to another anatomical location. If this decision is made, the array may remain on the target tissue 70 and the controller 110 or surgeon will trigger the diagnostic energy source 20D to ablate the tissue even though it has a normal fingerprint in it.

The diagnostic ablation can be done, for example to diagnose an anomalous tissue lying beneath the normal tissue. This step is particularly important when diagnosing and treating at the edges of abnormal masses to ensure the entire abnormality is removed. During this procedure, for example, the fingerprint of the denatured tissue is used to determine normalcy or normalcy based on tissue that has been ablated one or more times. For example, with basal cell carcinomas the malignant lesion can be hidden by normal tissue on the surface while malignant tissue is growing underneath. Some anomalous tissue may be known to be entirely under one or more layers of normal tissue requiring the normal tissue first to be removed to access the anomalous tissue. After ablating the normal target tissue 70, the medical device may then proceed to diagnose adjacent normal tissue. As used herein, normal target tissue can be normal tissue or denatured normal tissue. As noted, whether to move to a new target tissue site or ablate the normal tissue can be decided by the surgeon before or during treatment and can also be determined by the surgeon before ordering treatment. It is contemplated that the robotic controller 110 can be programmed with specific dimensions or with a specific sequence of steps described above. A non-limiting example of a programmed event is the continued diagnosis/treatment until reaching a non-limiting 300 micron anomalous tissue free zone 200 as shown in array of FIG. 7. A non-limiting example of a specific sequence might be repeating the therapeutic sequence three times after anomalous fingerprints and before performing another diagnosis. Any combination of diagnosis and therapeutic and diagnostic ablation therapy can be programmed into the controller 110 and used by one skilled in the surgical art. It is also contemplated that the surgeon can determine the necessary sequences during treatment or override programmed sequences as required. Alternatively, a triggering device within or connected to the controller 110 can initiate the necessary sequence based on preprogrammed information. Further, means may be provided for disabling the second or therapeutic source when normal tissue is detected without displacements of the diagnostic excitation radiation.

The display monitor 130 shown in FIG. 2 can be utilized for several options. Non-limiting examples of its uses included viewing the fingerprints, displaying the operating parameters, providing real-time information as to the duration of treatment, or patient information. It may also be in some instances used by the surgeon to manipulate the probe, or the joystick of the manually operated microscopic display as well as viewing the procedure as being performed robotically with or without input from the remote super database 140.

The probe 40 or the microscopic array of confocal microscope 50 of device 10 can be manually driven by the surgeon during treatment to the anomalous tissue with or use of the monitor 130. Due to the small-scale precise nature of the treatment the arrays of the probe 40 or microscope 50 can also be robotically driven. For example a robot or rastering mechanism can be utilized and driven by 110 to precisely control the location of the array. During the treatment process the robot mechanism can also be, for example, an articulated robotic arm. Alternatively, the robotic device can be an optical scanner raster. These robotic devices are provided by way of example and not limitation, and other robotic apparatuses known in the art can be used to control the movement of the arrays.

In one embodiment the probe 40 can be configured to almost contact the target tissue. This may require a disposable clear lens (not shown) capping the distal end of the probe preventing debris from absorbing the energies. A lens such as this may be appropriate for the distal lens system of the microscopic delivery system. Protective windows could be made of quartz (fused silica). Sapphire or any other suitable material, and should be easily removable and easily cleaned or replaced as desired.

In another embodiment the probe 40 can also contain an inert gas catheter (not shown) that can deliver positive pressure of air, nitrogen, or other gas through a lumen at the distal end of the probe 70 or through an inert gas catheter that can protect the environment and the probe tip from debris. As used herein, the "plume" is any material resulting from the ablation of the tissue such as Raman scatter 75, a plume of smoke, blood, ablative tissue remains, and other fluids. Provision for irrigation of the tissue site as well as known aspiration provisions by vacuum with attached collecting chamber are contemplated but not shown.

Another embodiment would have a combined excitation/ ablation/scatter detection path in the same fibers 35DTA as seen. In order to accommodate this coaxial orientation a dichroic beam splitter is used to combine the optical paths. The wavelength of the exciter emission and therapeutic emission would to be the same, and by way of example only, could be 532 nm emission such as produced by frequency doubled Nd:YAG lasers and blue or KTP (potassium titanyl phosphate lasers. Resonance Raman diagnostic emission would be pulses of approximately but not limited to 7 mW of power while therapeutic power would be high peak power pulses with power such as but not limited to 1000 Watts.

Figure 4:
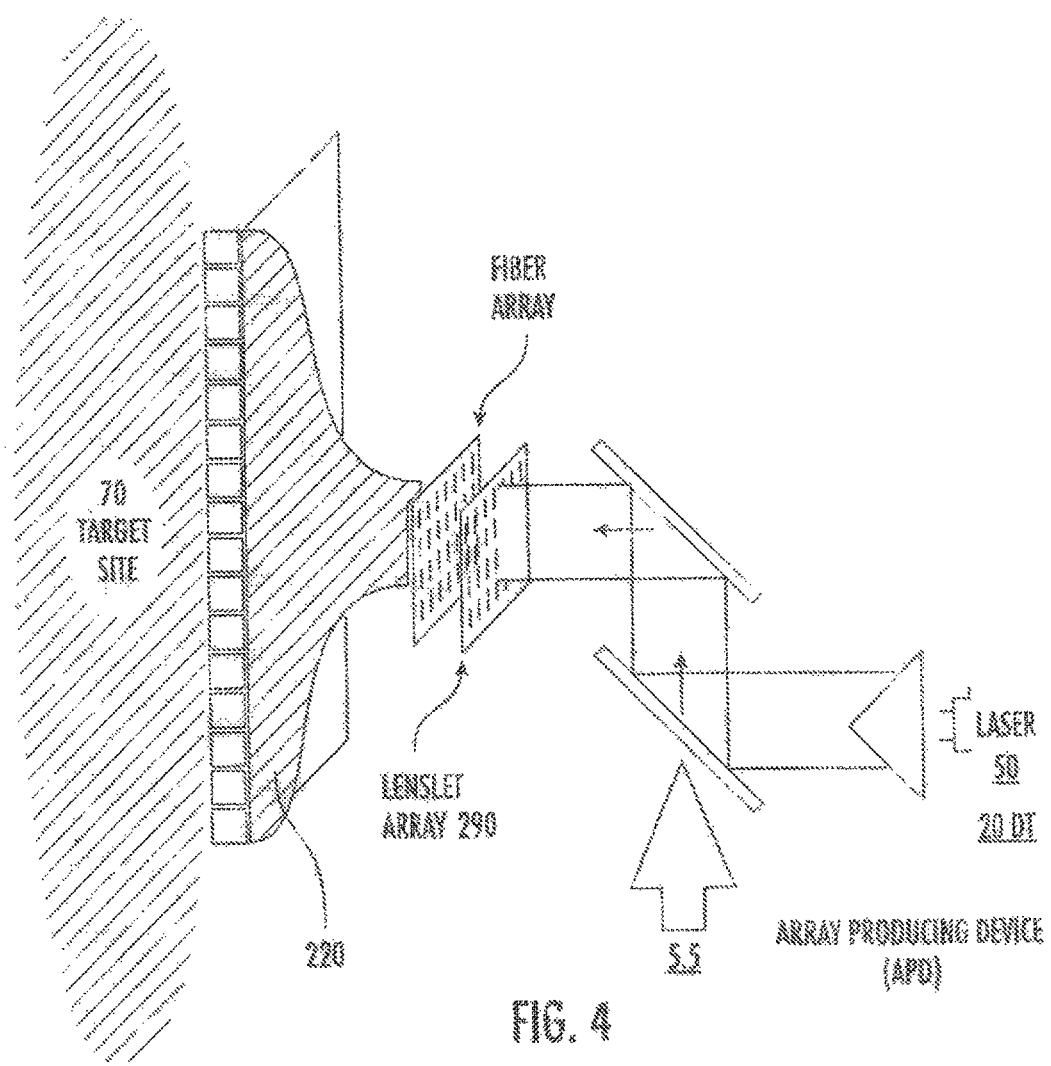
FIG. 4 depicts the rasterized image formed by an array forming device of a diagnostic array at the site of laser treatment by either a probe or confocal microscopic projection of the energies and demonstrates the use of two different patterns of coaxial exciter/sensor display and tracking patterns to delineate anomalous tissue and remove it while creating a clear tissue zone around the lesion.
Figure 5:
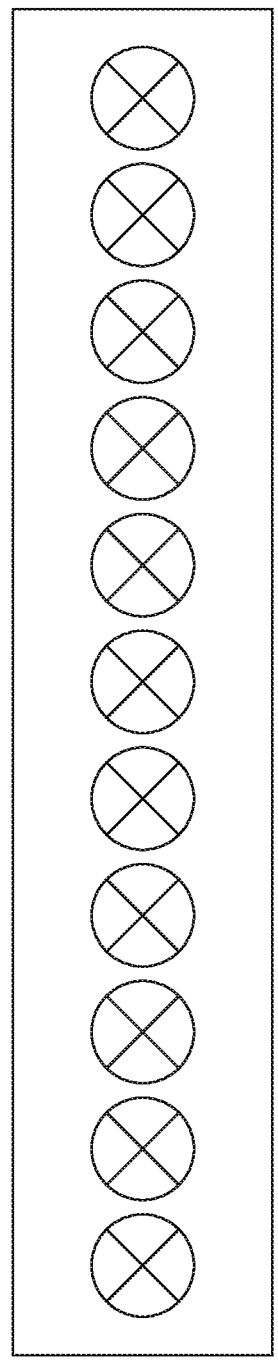
FIG. 5 is a schematic of two-dimensional array as it is represented in a computer/controller.

In another embodiment, the surgical microscope such as, but not limited to, a Zeiss OPM1 6 could be modified to accept all of the conduits and their variations as outlined in the above probe embodiments, wherein energy from the diagnostic exciter source 20D, and 20T therapeutic source could be merged into arrays such as seen in FIGS. 4, 5, and 7, passing through appropriate filters and focus onto the target site. Provision could be made for manual joystick operation of the beam as well as robotic control. Sensor/collector fibers at the distal end would be parfocal with the projected exciter/therapeutic arrays.

In another embodiment, all of fibers excitation, therapeutic, and sensor/collector fibers could be between but not limited to 10 to 350μ from the tissue. In another embodiment, therapeutic energy could be parfocal and focused on the exciter/sensor target site when moved with the target site under manual or robotic control.

In another embodiment of device 10 the system can be combined with other diagnostic modalities such as, but not limited to, optical coherence tomography (OCT), reflective confocal microscopy, MRI, or ultrasound to initially localize and grossly delineate the lesion, whereupon other surgical modalities such as, but not limited to, conventional surgery, electro-surgery, laser surgery, radiofrequency surgery, and cryosurgery can be used to rapidly debulk the lesion as visualized by eyesight or the above-mentioned diagnostic modalities. Debulking is the reduction of as much of the bulk (volume) of a tumor as possible. It is usually achieved by surgical removal. This process would then be augmented by the device 10 which could then remove the remaining surrounding area of residual anomalous tissue using resonance Raman guided laser ablation to obtain total anomalous tissue removal with a surrounding zone free of anomalous tissue.

In another embodiment of the probe 40 or microscope 50 used in device 10, there may be utilized a hollow articulated arm or waveguide such as that used to carry an emission such as, but not limited to, infrared carbon dioxide laser (10.6 micron) from energy source 20 T, that could contain ablative energy as well as the diagnostic/excitation energy from the source 20D as well as the scatter sensing fiber 85.

As seen in FIGS. 1 and 2, there is depicted the route by which the Diagnostic energy 20D and therapeutic energy 20 T are delivered to the target site 70.

Upon identification of the prospective target site 30 in tissue 120 an exciter pulse of energy such as but not limited to approximately 3.5 to 7 mW of 532 nm or 785 nm energy with an on time of 1 second is produced by an appropriate laser or LED is created in the resonance Raman exciter source 20 D and is conveyed by fiber-optic 50 through lens 820. Stray energy 825 which may be produced by the fiber-optic itself is filtered out at this point by lens filter 820. The energy produced is arrayed in a preselected pattern by the array producing device 30 as seen in FIGS. 4, 5, 7 and 8. Other patterns can be produced also. The pattern is then displayed by the confocal microscope 50 or into the probe 50 to be focused by lens 60 onto the tissue 120 where the targeted skin 30 or other appropriate tissue is to be diagnosed and presumably treated by the ablative laser such as but not exclusively pulsed carbon dioxide laser, if necessary. The invention also contemplates the use of a low energy source of UVC radiation, to genetically modify or destroy/remove organic micro-organisms including but not limited to viruses on or below the surfaces of tissues[9]. The ablative energy is carried within the lumen of cable 35DTA by fiber-optic or other suitable waveguide surrounded by the pattern formed by the exciter 20 fibers which may be separate from fibers that will eventually carry Raman scatter 95 to the spectrometer, or may be themselves coaxial with the Raman scatter sensor fibers. All energies with the exclusion of 825 pass through lens/filter 820 In conduit 25DT Into the array forming device 30, FIGS. 1, 4 and 5 and thence by conduit 35DTA to the confocal microscope 50 or probe 40. The exciter energy is focused and creates resonance Raman scatter 75 at the target site 70 and this scatter passes through filters 335 and 345 to the Sensor 80 FIG. 2. Lens 335/345 is coated to transmit Raman scatter energy and reject any reflected exciter energy emission trying to return as well as any ablative energy that could be contributing to noise. Pure Raman Scatter emission 95 is relayed to the spectrometer 90 which then communicates by cable 105 with the computer and database 110. Should the computer confirm the tissue fingerprint FIG. 9. to be anomalous it relays the data through conduit 115 to the robotic display controller 110 or if under manual control directly to the ablative laser manual control 150 by fiber 155. All the connections could be wireless. This initiates a pulse of energy from the ablating laser source 20T which carries the energy in the central portion of cable 25T by way of fiber-optic or waveguide filter 820 and through conduit 25 DT through or around the array forming device to probe 40 or confocal microscope then through the focusing lens 60 resulting in vaporization of the target site 70. This process is performed repeatedly either robotically or manually under direct visualization, by visualization of the site through the monitor 130 or through the confocal operating microscope 50.

[9] Reference 22

It can also be done by communication from the computer 100 through connector 115 to the robotic display controller 110, which can direct the firing of the ablating laser source 20D by cable 165 Diagnosis/therapy is performed until all anomalous tissue isablated or removed as seen in FIGS. 7 and 8 leaving a clear tissue zone circumscribing the perimeter of the removed anomalous tissue. Since this invention is at first concerned mostly with skin lesions, the preferred embodiment is: to have the exciter/sensor fibers coaxially arranged in a linear pattern as shown in FIGS. 4 and 8. Starting at the center of the visually observed lesion FIG. 8, 120 using the array as seen in FIGS. 4, 5, 7 and 8 is initiated on area 120 through the confocal microscope system 50, the Raman scatter is collected by the sensor fibers where aberrant energy from the impact site is filtered by filter 335/345 and transmitted to the sensor 80 and thence by conduit 95 to the spectrometer 90. Since all vertically arranged fibers are positive for anomalous tissue after the fingerprints FIG. 9. are adjudicated by the CPU 100, a signal is sent through the robotic controller 110 to repeat the ablation/diagnostic episodes until the deep tissue is all clear. The probe is then moved toward a visually presumed periphery 210 and the process is repeated until by way of example area 270 is reached where the only positive sensor readings 250 are in the central area of the ablation site 70 and at least 6 (300 microns) 260 are free of anomalous tissue.

The CPU then directs the robotic controller 110 to move the display laterally keeping the configuration the same as seen in FIG. 7 creating a path of treatment around the lesion with a clear zone 200 surrounding it.

In another embodiment, fiber lasers, diode lasers, could be utilized to create more accurate and efficient diagnosis and therapy.

In another embodiment, a camera may be incorporated into the medical device 10 to capture images of target tissue. The camera can be conventional digital or video as desired or required.

In another embodiment, LEDs of appropriate wavelength configured in similar arrays as in FIGS. 4, 5, 7 and 8 with sensor/collector fibers could be fitted underneath the microscope in a separate carriage (Not shown).

Seen in FIG. 8 array 260 could be used. Coaxial fibers could be used These fibers are arranged in a square quadrantically 260 for representation on the spectrometer 90 and CPU 100 They are projected onto the perimeter of the lesion and by rasterized control by the robotic controller, by example along a track 220 either vertically or horizontally to remove the anomalous tissue in the same manner as has been described with repetitive diagnostic and ablative pulses until all anomalous tissue is vaporized as seen in FIG. 8, leaving a clear tissue zone 200 circumscribing the perimeter of the removed anomalous tissue. This process can be performed to create a clear zone FIG. 3 200 enhancement of anomalous tissue grossly delineated by imaging entities such as but not limited to MRI and OCT and treated with debulking entities, such as but not limited to conventional surgery, laser surgery, cryosurgery, electro-surgery, radiation therapy or chemotherapy. This data can be communicated by an accessory device by the cable 135 to the CPU 100.

Different displays of fibers can be used such as but not limited to FIGS. 8 250 and 260 depending on whether the initial topography of the visually anomalous tissue is defined from the center of the lesion outward or from the periphery inward. Other Tracking patterns can be used, as seen but not limited to, in FIGS. 8, 250 and 260.

The pattern of the peripheral clear zone of the lesion seen in FIG. 8 perimeter 210 can be saved in the computer 100, and be used by use of the robotic controller 110 to create a custom fitted skin graft to repair the defect created by the anomalous tissue removal.

In another embodiment of the probe 40 or microscope 50 used in device 10, there may be utilized a hollow articulated arm or waveguide such as that used to carry an emission such as, but not limited to infrared carbon dioxide laser (10.6 micron) from energy source 20 T which could contain ablative energy as well as the diagnostic/excitation energy from source 20 D as well as the scatter sensing fiber 95. A number of conduits and fibers could be configured to create the most efficient system.

In another embodiment the exciter/sensor collector fibers are separate and the therapeutic fibers or waveguide are used in a different wavelength such as, but not limited to a high-powered pulsed carbon dioxide laser energy (10.6 micron) delivered parfocally to the target site.

In another embodiment the exciter fibers and the sensor collection fibers are discrete within the bundle in a pattern creating an array such as seen in FIGS. 5, 7 and 8.

In another embodiment, the exciter fibers and the therapeutic fibers are the same and the sensor collector fibers are separate within conduit 85.

In another embodiment, the exciter, sensor collector, and therapeutic conduits are all separate within the bundle 35DTA.

In another embodiment, agents such as, but not limited to methylene blue, derivatives of amino levulinic acid, talaporfin, and some precious metals could be given to patients to expedite diagnosis and/or treatment should the risk/benefit ratio warrant it.

Embodied Arrays of Diagnostic/Exciter Energy and their Usage and Strategies for Successful Treatment of Anomalous Tissue with Device 10

The goals of this invention are to remove unwanted anomalous tissue, while preserving the adjacent normal tissue. The gold standard for determining the difference in these two tissues has been histopatholgy. Optical biopsy with systems such as resonance Raman spectroscopy are now coming forward to represent a future alternative method. Up to now, regular Raman spectroscopy as well as other modes of optical biopsy have been unable to create the differentiation of tissues quickly enough to make optical biopsy guided treatment of the abnormal tissues feasible. With the availability of ultrafast techniques such as but not limited to resonance Raman spectroscopy with its ability to create a fingerprint in 1 second or less, the device herein 10 has become feasible. Conventional surgery, requires repeated histopathologic examination to determine whether margins of anomalous tissue removal are clear of the anomalous tissue and are time-consuming and often because of location, difficult to determine, and sometimes inaccurate. Most forms of therapy that are not performed by conventional surgery are additionally encumbered by concerns that the modalities themselves destroy the interface between the normal and abnormal tissue rendering histopathologic diagnosis of the anomalous tissue margin even more difficult. Herein we present specially designed arrays and patterns to be used in probes and probe-like devices or microscopic delivery systems that will create anomalous tissue clear zones with non-limiting strategies for their use. All arrays can be designed with energy sources, such as but not limited to, lasers or LEDs, and can be within or attached to either probe-like devices such as, but not limited to dermatologic probes, bronchoscopes, laparoscopes, endoscopes, cystoscopes as well as operating microscope's, and Raman spectrometer microscopes.

The first decision needed for strategy is whether to approach the anomalous tissue to be treated from its visualized or imaged center and work toward the surrounding normal tissue, or to create a periphery of normal tissue with a substantial clear zone and work toward the center of the issue. This need be done both horizontally and in depth. Fibers arrayed in FIG. 8 in which display 250 is linear illustrates how the vertical probe pattern moves it from the center to the periphery where it upon finding a site 270 of clear tissue begins to move by manual or robotic control as shown in FIG. 8 to define a clear periphery 200.

Array 260 which is square and quadrantic can be moved by example from the visual periphery with DTA sites arrayed quadrantically into the CPU 100 for additional guidance in movement to the controller 110 into the visible tumor mass on track 220 The arrays will then be manually or robotically guided to remove abnormal tissue as it establishes a rough perimeter within the confines of the established visual perimeter. It should be noted that the array would then be adjusted to a site at the periphery 270 where it or the 250 array would produce a new track of the periphery 270 with a 300 Micron anomalous issue clear zone. The width of the clear margin desired could be a surgeon decision or a database decision, as would be the power, wavelength, and on time of the energy source. In some instances, where deemed feasible, this pattern of tissue removal 210 would be stored in the database and used to create a custom graft as needed.

In an alternative embodiment, if it seems prudent, debulking of the lesion is facilitated by vision, or an imaging system such as MRI, ultrasound or other modality known in the art. Then performed surgically, with cryotherapy, electro-surgery, radiation, or any other modality as used in the art. Another useful embodiment of the device would be utilizing the arrays to guide laser therapy to discover and remove residual anomalous tissue. Varying tracking patterns would be available from the computer software, as well as the ability to manually create tracking patterns. FIG. 8.

Provision for debulking lesions previously grossly imaged by other imaging methods such as OCT, MRI, auto or induced fluorescence, or similar entities will be made utilizing the components and appropriate wave lengths, spot sizes and energy levels. Finishing areas previously debulked by devices such as conventional surgery, electro-surgery, cryosurgery, chemotherapy, radiation therapy, and genetic therapy, may be performed, aided by the multi-centered super online data base 140 by conduit 135, the robotic controller 110 through conduit 115.

While the invention has been shown and described with reference to certain embodiments thereof, it will be understood by those skilled in the art that various changes in form and detail may be made therein without departing from the spirit and scope of the invention as defined by the appended claims and their equivalents.

The invention claimed is:

1. A medical device for diagnosing and treating anomalous tissue comprising
   a first source for directing an array of diagnostic excitation radiation at a tissue target site to produce resonance Raman scattering (RRS);
   a second source for directing an array of treating or therapeutic radiation at the tissue target site to produce ablation of tissue;
   fiber optic or waveguide light conduits arranged in a pattern to deliver said array of excitation radiation and said array of treating or therapeutic radiation to the tissue target site;
   detecting means for detecting said RRS at said target site when diagnostic excitation impinges on the tissue;
   determining means for determining whether said detected RRS is indicative of anomalous tissue; and
   activation means for activating said second source to direct the array of treating or therapeutic radiation at the tissue target site to ablate the tissue target site only when the tissue target site is determined to be anomalous to create a peripheral clear zone circumscribing a lesion at the tissue target site.

2. A medical device as defined in claim 1, wherein said first source emits radiation having a wavelength for producing RRS in organic molecules including excitation radiation having a wavelength approximately equal to 532 nm.

3. A medical device as defined in claim 1, further comprising directing means for propagating said excitation radiation to selected portions of the tissue at the target site.

4. A medical device as defined in claim 3, wherein said directing means includes a probe.

5. A medical device as defined in claim 3, wherein said directing means includes a confocal microscope.

6. A medical device as defined in claim 3, wherein said fiber optic or waveguide light conduits are interposed between said radiation sources and said directing means.

7. A medical device as defined in claim 3, further comprising means for moving said directing means over at least portions of the target tissue within said peripheral clear zone.

8. A medical device as defined in claim 7, wherein said directing means includes means for directing said radiations along tracks within said peripheral clear zone until the entire area therein has been analyzed.

9. A medical device as defined in claim 1, wherein said detecting means comprises a sensor for sensing said RRS and a spectrometer for analyzing said RRS to establish a detected fingerprint identifying the nature of the tissue.

10. A medical device as defined in claim 9, wherein said determining means comprises a computer and a database stored on said computer containing at least one reference fingerprint associated with an anomalous tissue, said computer being programmed to compare said detected fingerprint against said at least one reference fingerprint in said database.

11. A medical device as defined in claim 10, wherein said computer is programmed to control a robotic controller to move to next adjacent areas of the targeted tissue if the tissue is determined to be normal or ablate to a depth of anomalous tissue until normal tissue is detected.

12. A medical device as defined in claim 9, wherein a fiber optic or waveguide light conduit transmits the RRS to said sensor.

13. A medical device as defined in claim 1, further comprising a robotic controller programmed to repeatedly actuate said first source.

14. A medical device as defined in claim 13, further comprising a probe or confocal microscope for propagating said excitation radiation to selected portions of the tissue at the target site and a robot system responding to the controller, and configured to move the probe or confocal microscope in relationship to the tissue, wherein the controller is programmed and repeatedly actuates the first source to emit the excitation radiation; and in response to a control signal, actuate the second source of the treating or therapeutic energy, and then actuate the the robot system to move the probe or the confocal microscope.

15. A medical device as defined in claim 1, wherein said activation means includes a controller and further comprising a robot system responding to said controller and configured to move a probe or confocal microscope in relationship to the tissue, wherein the controller is programmed to repeatedly actuate said sources to emit said diagnostic excitation radiation; and in, response to a control signal, emit said treating or therapeutic radiation to initiate ablation modes and then move either the probe or the microscope arrays to a next successive portion of the tissue.

16. A medical device as defined in claim 1, wherein said fiber optic or waveguide light conduits are arranged to form an array of optical fibers that expose a predetermined portion of the target tissue to said radiations.

17. A method of diagnosing and treating anomalous tissue comprising the steps of
   directing an array of diagnostic excitation radiation at a tissue target site with fiber optic or waveguide light conduits arranged in a pattern to produce resonance Raman scattering (RRS);
   directing an array of treating or therapeutic radiation at the tissue target site with the fiber optic or waveguide light conduits arranged in a pattern to produce ablation of tissue; detecting said RRS at said target site when diagnostic excitation impinges on the tissue; and
   determining whether said detected RRS is indicative of anomalous tissue;
   wherein directing treating or therapeutic radiation at the tissue target site to ablate the tissue target site is performed only when the tissue target site is determined to be anomalous to create a peripheral clear zone circumscribing a lesion at the tissue target site.

18. A method as defined in claim 17, further comprising using a robot system to successively move arrays of said radiations in a programmed manner in relationship to the tissue target site to repeatedly expose successive portions of the tissue within the peripheral clear zone to emit said diagnostic excitation radiation; and in response to a control signal, emit said treating or therapeutic radiation and then move said arrays to a next successive portion of the tissue target site until the entire area within said peripheral clear zone has been examined and treated.

19. A method as defined in claim 18, comprising the step of removing of anomalous tissue previously treated in any conventional way including laser surgery, cryosurgery, electrosurgery, radiation or chemotherapy.

\* \* \* \* \*